United States Patent
Hong et al.

(10) Patent No.: US 9,540,614 B2
(45) Date of Patent: Jan. 10, 2017

(54) METHOD FOR GENERATING CANCER STEM CELLS FROM IMMORTALIZED CELL LINES

(71) Applicant: KOREA UNIVERSITY RESEARCH AND BUSINESS FOUNDATION, Seoul (KR)

(72) Inventors: Sunghoi Hong, Seoul (KR); Seung-Ick Oh, Seoul (KR); Hang-Soo Park, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 14/222,697

(22) Filed: Mar. 24, 2014

(65) Prior Publication Data

US 2015/0104864 A1    Apr. 16, 2015

(30) Foreign Application Priority Data

Oct. 11, 2013   (KR) .......................... 10-2013-0121609

(51) Int. Cl.
*C12N 5/095*    (2010.01)
(52) U.S. Cl.
CPC ..... *C12N 5/0695* (2013.01); *C12N 2502/1358* (2013.01); *C12N 2506/25* (2013.01); *C12N 2510/04* (2013.01)

(58) Field of Classification Search
None
See application file for complete search history.

(56) References Cited

FOREIGN PATENT DOCUMENTS

| KR | 1020070111570 A |  | 11/2007 |  |
|----|----|----|----|----|
| KR | 100783199 B1 |  | 12/2007 |  |
| KR | 1020120099904 A |  | 9/2012 |  |
| KR | 10-2011-0044267 | * | 11/2012 | ........... C12N 5/0797 |
| KR | 101242726 B1 |  | 3/2013 |  |

OTHER PUBLICATIONS

Debeb et al., Characterizing cancer cells with cancer stem cell-like features in 293T human embryonic kidney cells, Molecular Cancer, 2010, vol. 9:180, pp. 1-12.*
GE Healthcare, GE Healthcare, Hyclone Classical Liquid Media, DMEM F12 with 2.50mM L-Glutamine, 15mM HEPES, retrieved from the internet, Sep. 2, 2015: shop.neobits.com/ge_healthcare_sh30023_01_hyclone_classical_liquid_media_dmem_f12_with_2_50mm_l_glutamine_15mm_hepes_each_500ml_1032779208.php.*
Gibco, GlutaMAX I (100X), Jun. 2003, retrieved from the internet: web.mit.edu/rkarimi/www/Special/Other/Protocol/Cell%20Culture/Glutamax%20supplement.pdf.*
Jin et al., Comparison Between Cells and Cancer Stem-Like cells isolated from Glioblastoma and Astrocytoma on Expression of Anti-Apoptotic and Multidrug Resistance-Associated Protein Genes, Neuroscience, vol. 154, 2008, pp. 541-550.*
Nishimura et al., Mesenchymal Stem Cells Provide an Advantageous Tumor Microenvironment for the Restoration of Cancer Stem Cells, Pathobiology, published online Jun. 9, 2012; 79: pp. 290-306.*
Schneider et al., Complex Cellular Responses of Helicobacter pylori-Colonized Gastric Adenocarcinoma Cells, Infection and Immunity, Jun. 2011, vol. 79, No. 6, pp. 2362-2371.*
Oka et al., 293FT cells transduced with four transcription factors (OCT4, SOX2, NANOG, and LIN28) generate aberrant ES-like cells, Journal of Stem Cells & Regenerative Medicine, 2010, vol. 6 Issue 3, pp. 149-156.*
Marshall et al., Gene Knockout Protocols, Humana Press, 2001, Isolation and Maintenance of Primate Embryonic Stem Cells, Methods in Molecular Biology, vol. 158, pp. 11-18.*
Yu et al., Essentials of Stem Cell Biology, $2^{nd}$ Edition, 2009, Induced Pluripotent Stem Cell Derivation, pp. 331-332.*
Oh, Seung-Ick, "Conversion of immortalized cells to cancer stem cell-like cells", Jun. 12-15, 2013, Poster Abstracts, International Society for Stem Cell Research (ISSCR), 11th Annual Meeting.
Castellone, M., et al., "Brief report: Mesenchymal stromal cell atrophy in coculture increases aggressiveness of transformed cells", "Stem Cells", Jun. 2013, pp. 1218-1223, vol. 31.

* cited by examiner

*Primary Examiner* — Thane Underdahl
*Assistant Examiner* — Yvonne Pyla
(74) *Attorney, Agent, or Firm* — Hultquist, PLLC; Steven J. Hultquist

(57) ABSTRACT

A method is described for generating a novel cancer stem cell line that possesses characteristics associated with stem cells, by co-culturing a human immortalized cell line and bone marrow-derived mesenchymal stem cells, and the novel cancer stem cell line established thereby. This method is able to readily generate cancer stem cells that are low in the level of structural chromosomal aberrations and are excellent in oncogenicity, and is effectively applicable to the development of anti-cancer drugs and personalized drugs.

10 Claims, 23 Drawing Sheets

FIG. 8B

| | Injected cells | Outgrowths/ Injection | Frequency |
|---|---|---|---|
| iCSC1 (Unsorted) | 5 × 10⁶ | 3/3 | |
| | 1 × 10⁶ | 3/3 | |
| | 5 × 10⁵ | 6/6 | |
| | 1 × 10⁴ | 6/6 | 1/133 |
| | 1 × 10³ | 6/6 | (1/33 ~ 1/548) |
| | 1 × 10² | 1/3 | |
| | 1 × 10¹ | 1/3 | |
| CD15⁺ | 1 × 10⁴ | 3/3 | |
| | 1 × 10³ | 3/3 | 1/134 |
| | 1 × 10² | 1/3 | (1/32 ~ 1/571) |
| | 1 × 10¹ | 1/3 | |
| CD15⁻ | 5 × 10⁵ | 3/3 | |
| | 1 × 10⁴ | 1/3 | 1/28,004 |
| | 1 × 10³ | 0/3 | (1/3,974 ~ 1/197,381) |
| | 1 × 10² | 0/3 | |
| 293FT | 1 × 10⁴ | 0/3 | -Inf |
| | 1 × 10³ | 0/3 | (1/11,016 ~ -Inf) |

$p = 0.995$
$p = 2.36e-9$
$p = 1.71e-11$

METHOD FOR GENERATING CANCER STEM CELLS FROM IMMORTALIZED CELL LINES

CROSS-REFERENCE TO RELATED APPLICATION

The priority of Korean Patent Application no. 10-2013-0121609 filed Oct. 11, 2013 is hereby claimed under the provisions of 35 USC 119. The disclosure of Korean Patent Application no. 10-2013-0121609 is hereby incorporated herein by reference, in its entirety, for all purposes.

BACKGROUND OF THE INVENTION

Field of the Invention

The present invention relates to a method for generating a cancer stem cell line from an immortalized cell line. More particularly, the present invention relates to a method for generating a novel cancer stem cell line that possesses characteristics associated with stem cells, by co-culturing a human immortalized cell line and bone marrow-derived mesenchymal stem cells, and the novel cancer stem cell line established thereby.

Description of the Related Art

Cancer stem cells (hereinafter referred to as "CSCs", interchangeably used for tumor stem cells) are primary tumor cells that exhibit self-renewal, proliferative capacity and multi-differentiation, forming a microenvironment where blood vessels, mesenchymal stem cells and a variety of cancer cells are found. Now, there are four methods of isolating cancer stem cells from tumor tissue using characteristics of cancer stem cells:

first, MACS (Magnetic-Activated Cell Sorting) and FACS (Fluorescence-Activated Cell Sorting), using antibodies against specific markers expressed by tumor stem cells;

second, side population discrimination by a dye exclusion assay that takes advantage of the high activity of an ABC reporter predominantly in leukemia and multiple myeloma;

third, isolation using the activity of such enzymes that are overexpressed in tumor stem cells as aldehyde dehydrogenase (ALDH); and fourth, segregation of tumor stem cells from differentiated cancer cells by forming a tumorsphere in the presence of growth factors (EGF and bFGF) in a serum-free medium.

These methods, although readily isolating CSCs from cancer cells, are not effective in securing a multitude of CSCs since the CSCs are different in ratio from each other. Also, the CSCs isolated by each isolation method differ in oncogenesis from one to another. In addition, since characteristics of CSCs are changed during cultivation, isolation and culture methods are further studied. Moreover, it takes a significant time to obtain tumor tissues from cancer patients according to legal and administrative matters.

Hence, there is a need for a method for generating cancer stem cells that overcomes the conventional problem of isolating a small population of cancer stem cells and that can secure a multitude of homogenous cancer stem cells, with few legal or administrative limitations.

As a background of the present invention, Korean Patent No. 10-1242726 (issued Mar. 13, 2013) discloses a method of diagnosing cancer with a cancer stem cell property by measuring the expression level of aldehyde dehydrogenase (ALDH). Korean Patent Publication No. 10-2012-0099904 (issued Sep. 12, 2012) describes a tumor stem cell-targeting peptide GICT that can selectively recognize and bind malignant, undifferentiated glioma cells, and a method for diagnosing encephaloma. Korean Patent No. 10-0783199 (issued Dec. 6, 2007) describes a cancer stem cell line GBM 2, established from human glioblastoma multiforme tissue, having resistance to drugs.

However, nowhere is a method of easily, quickly and efficiently generating cancer stem cells from an immortalized cell line and maintaining the cancer stem cells found in previous literature.

Leading to the present invention, intensive and thorough research into the mass production of cancer stem cells having high oncogenic potential resulted in the finding that cancer stem cells can be derived from an immortalized cell line which is co-cultured with mesenchymal stem cells.

References relevant to the subject matter of the present disclosure include the following:

In vitro generation of human cells with cancer stem cell properties. Scaffidi P, Misteli T. Nat Cell Biol. 2011 Aug. 21; 13(9):1051-61.

SSEA-1 is an enrichment marker for tumor-initiating cells in human glioblastoma. Son M J, Woolard K, Nam D H, Lee J, Fine H A. Cell Stem Cell. 2009 may 8; 4(5):440-52

CD133, CD15/SSEA-1, CD34 or side populations do not resume tumor-initiating properties of long-term cultured cancer stem cells from human malignant glio-neuronal tumors. Patru C, Romao L, Varlet P, Coulombel L, Raponi E, et al., BMC Cancer. 2010 Feb. 24; 10:66.

The micro-RNA 199b-5p regulatory circuit involves Hest, CD15, and epigenetic modifications in medulloblastoma. Andolfo I, Liguori L, De Antonellis P, Cusanelli E, Marinaro F, Pistollato F, Garzia L, et al., Neuro-Oncology. 2012 Jan. 22; 14(5):596-612.

SUMMARY OF THE INVENTION

It is an object of the present invention to provide a method for generating a cancer stem cell line from an immortalized cell line.

It is another object of the present invention to provide a cancer stem cell line generated using the method.

It is a further object of the present invention to provide a culture medium for use in inducing a cancer stem cell line from an immortalized cell line.

To achieve the above objects, the present invention provides a method for generating a cancer stem cell line from an immortalized cell line, comprising: co-culturing an immortalized cell line and mesenchymal stem cells in an induction medium, with the mesenchymal stem cells serving as feeder cells.

Also, the present invention provides the cancer stem cell line generated using the method.

Further, the present invention provides a culture medium for inducing a cancer stem cell line from an immortalized cell line, comprising mesenchymal stem cells, and high-glucose DMEM supplemented with FBS, L-glutamine, and L-alanyl-glutamine.

BRIEF DESCRIPTION OF THE DRAWINGS

The above and other objects, features and other advantages of the present invention will be more clearly understood from the following detailed description taken in conjunction with the accompanying drawings, in which:

FIG. 1A shows the fibroblast-like morphology of bone marrow-derived mesenchymal stem cells (early passage, P3) (magnified 100 times);

FIG. 1B shows the identification of the cells used in an experiment as mesenchymal stem cells (>98%), as analyzed by FACS using stem cell-specific surface markers (positive markers; CD29, CD73, CD90, CD105, HLA-ABC, negative markers; CD14, CD34, CD45);

FIG. 2A is a schematic view illustrating a protocol for inducing cancer stem cells from a human immortalized cell line;

FIG. 2B shows cells induced from the human immortalized cell line (293FT) during the procedure of the protocol (magnified 40 times);

FIG. 2C shows cancer stem cell lines (iCSC1, iCSC2) derived from human immortalized cell line (293FT) (magnified 100 times);

FIG. 2D shows induction efficiencies of cancer stem cells from various human immortalized cell lines (HEK293, 293T, 293FT, Dermal papilloma, Neural stem cell) and cancer cell lines (L-132, U87, SW480, A549, HeLa), as analyzed by FACS using a cancer stem cell-specific marker (CD133);

FIG. 2E shows relative mRNA expression levels of CD133 (Prom1) in human immortalized cell line (293FT) and 293FT-derived cancer stem cells, as analyzed by real-time PCR;

FIG. 2F shows karyotype profiles of a human immortalized cell line (293FT) and 293FT-derived cancer stem cell lines (iCSC1, iCSC2);

FIG. 8B shows the oncogenicity of each of iCSC1 (unsorted), $CD15^+$, $CD15^-$ and 293FT cells subcutaneously injected to immunosuppressive mice (BALE/c nu/nu) (injected cells: No. of injected cells; outgrowths/injection: No. of tumor formed/No. of Injection; Frequency:Mean ratio of cancer stem cells present);

DESCRIPTION OF THE PREFERRED EMBODIMENTS

Figure 1A:
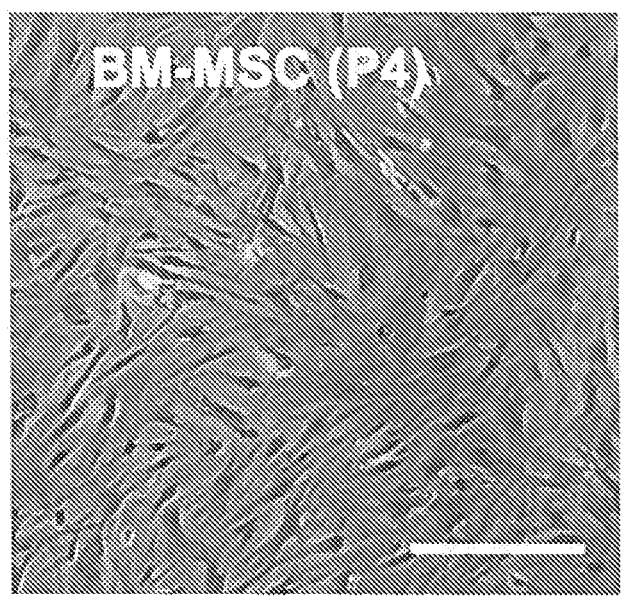
FIGS. 1A and 1B show characteristics of human bone marrow-derived mesenchymal stem cells.

Unless defined otherwise, all the technical and scientific terms used in the specification have the same meanings as understood to those ordinarily skilled in the art to which the present invention pertains. Generally, the nomenclature used in the specification is well known in the art and found in typical practice.

In accordance with an aspect thereof, the present invention addresses a method for generating a cancer stem cell line from an immortalized cell line, comprising: co-culturing an immortalized cell line and mesenchymal stem cells in an induction medium, with the mesenchymal stem cells serving as feeder cells.

The mesenchymal stem cells which serve as feeder cells in the present invention may be those isolated and purified from, but not limited to, the bone marrow, blood, cord blood, the periosteum, the dermis, and the mesoderm. Preferably, the mesenchymal stem cell may be bone marrow-derived mesenchymal stem cells (BMMSC). BMMSC refers to multipotent progenitors which can differentiate into cells of specific organs, such as bone, cartilage, fat, tendon, nerve tissues, fibroblasts, and muscle cells.

In a preferred embodiment of the present invention, the mesenchymal stem cells may be isolated from, but not limited to, human bone marrow. When monocytes isolated from the bone marrow are cultured for 1 to 2 weeks, almost all hepatopoietic stem cells are prone to differentiation and thus have differentiated into blood cells whereas the remaining cells capable of self-renewal can be readily isolated as mesenchymal stem cells. Alternatively, the monocytes isolated from the bone marrow may be cultured, and used per se as feeder cells, without conducting an additional process of isolating mesenchymal stem cells from the monocytes.

For use in the present invention, BMMSC may be commercially available. In one embodiment of the present invention, the feeder cells may be cultured to 80% or greater confluency in LONZA MSCBM (Mesenchymal Stem Cell Basal Medium) containing 10% MCGS supplement+2% L-glutamine+0.1% GA-1000 before application to the co-culturing with an immortalized cell line.

The immortalized cell line of the present invention may be obtained by genetically modifying normal cells. No particular limitations are imparted to the immortalized cell line, but an immortalized cell line of human origin is preferred. Immortalization may be realized by transformation, for example, by transfecting viral genes (E1A, SV40 Large-T antigen, etc.) into human somatic cells to inhibit the activity of tumor suppressors such as p53, pRb, etc., by introducing a telomerase reverse transcriptase gene into human somatic cells, or by overexpressing Ras and MYC genes. Like this, genetic modification may transform human normal cells to an immortalized cell line.

Turning now to the induction medium of the present invention, such medium is based on high-glucose DMEM characterized by a glucose concentration of 10~100 mM.

The basic medium for the induction medium may be artificially prepared or commercially available. The medium useful in the present invention is based on the DMEM (Dulbecco's Modified Eagle Medium, Life Technologies) in which the level of glucose is selectively increased. Preferably, but in a non-limiting manner, the medium of the present invention is based on high-glucose DMEM having a glucose concentration of 10 to 100 mM, and more preferably, a glucose concentration of 10 to 30 mM.

In a further embodiment, the induction medium may further comprise L-glutamin and L-alanyl-glutamine.

For use as the induction medium, the high-glucose DMEM may be supplemented with factors indispensible for cell growth, including serum, growth factors and/or antibiotics. Preferably and in a non-limiting manner, the medium may contain L-glutamine and L-alanyl-glutamine.

According to one embodiment of the present invention, high-glucose DMEM supplemented with 10% FBS, 2 mM L-glutamine, 4 mM L-alanyl-glutamine and 1% penicillin-streptomycin is used as the induction medium.

Together with mesenchymal stem cells, an immortalized cell line is co-cultured for 16 to 20 days, and preferably for 20 days.

Preferred examples of the immortalized cell line useful in the present invention include, but are not limited to, HEK293, and 293FT cells.

The co-culturing of the present invention may result in inducing the immortalized cells to undergo a reduction in accumulated structural chromosomal aberrations (chromosome instability) or an increase in the number of chromosomal aberrations.

In another embodiment of the present invention, a novel cancer stem cell with the characteristics of brain cancer stem cells can be derived from the immortalized cell line (293FT cell line, Invitrogen) which is co-cultured with human bone marrow-derived mesenchymal stem cells (BMMSC) as feeder cells. Preferably and in a non-limiting fashion, the cancer stem cell line may be a brain cancer stem cell line derived from 293FT. The brain cancer stem cells constitute a novel brain tumor stem cell line different from the parental cell line 293FT, and can be grown with FBS in both adherent and suspension culture patterns, showing an increased expression of neural stem cell markers, an improved ability to form neurospheres, and an increase in the expression of $CD15^+/CD133^+$ by up to 95% upon suspension culturing. In addition, the brain cancer stem cells are morphologically very similar to neural stem cells, exhibit a reduction in structural chromosomal aberration and an acquisition of tumorigenic ability, and can differentiate into various neural cells. Other than brain cancer stem cells, several kinds of cancer stem cells are found to exist, as analyzed for tissue-specific cancer stem cell markers by FACS, which leaves the possibility that various kinds of cancer stem cells could be isolated.

The cancer stem cell line of the present invention possesses at least one of the following characteristics:

(a) being immunologically positive to the neural stem cell markers CD15 (SSEA-1), CD56 (NCAM), CD29 (Integrin beta1), Nestin, CD133 (Prominin 1), CD24 (Small cell lung carcinoma cluster 4 antigen) and CXCR4 (chemokine (C-X-C motif) receptor 4); and negative to the mesenchymal stem cell marker CD73 (Ecto-5'-Nucleotidase) (refer to Table 1);

(b) no appearance of differentiated cells upon suspension culture;

(c) the appearance of dendrites, morphologically characteristic of neural cells, having round and streamlined nuclei that are large in comparison to whole cells in an FBS-supplemented medium;

(d) the oncogenicity that even as few as 10 cells can form tumor in immune-suppressed mice (BALE/c nu/nu); and (e) differentiation into neural cells in an induction medium.

TABLE 1

| | Expression Distribution of Markers for Neural Stem Cells | | | | | | | |
|---|---|---|---|---|---|---|---|---|
| Cell | CD15 | CD56 | CD29 | Nestin | CD133 | CD24 | CXCR4 | CD73 |
| iCSC1 | 90% | 77% | 72% | 61% | 10% | 3% | 97% | <0.1% |
| iCSC2 | 94% | 78% | 75% | 62% | 8% | 7% | 95% | <0.1% |
| 293FT-icsc | 4% | N.D. | N.D. | N.D. | 3% | N.D. | 81% | N.D. |

The cancer stem cell line is maintained for a long period of time by many passages in an adherent culture manner in a medium supplemented with FBS, or in a suspension culture manner in a medium devoid of FBS, but supplemented with bFGF and EGF.

Upon suspension culture, the expression of CD133, a marker for neural stem cells, is increased, making CD15$^+$/CD133$^+$ cells account for more than 90% of total cell counts.

Also, contemplated in accordance with another aspect of the present invention is the cancer stem cell line generated using the method.

In accordance with a further aspect thereof, the present invention relates to a culture medium for inducing a cancer stem cell line from an immortalized cell line, comprising mesenchymal stem cells, and high-glucose DMEM supplemented with FBS, L-glutamine, and L-alanyl-glutamine.

In another embodiment of the present invention, a cancer stem cell line was generated from an immortalized cell line in a medium including bone marrow-derived stem cells; and high-glucose DMEM having 20 to 30 mM glucose, supplemented with 8 to 10% FBS, 1 to 3 mM L-glutamine, and 3 to 5 mM L-alanyl-glutamine.

A better understanding of the present invention may be obtained through the following examples which are set forth to illustrate, but are not to be construed as limiting, the present invention.

EXAMPLE 1

Cell Culture and Expansion of Human Bone Marrow-Derived Mesenchymal Stem Cells

The bone marrow-derived mesenchymal stem cells (BM-MSCs) used in the present invention, purchased from the cell bank LONZA (Walkersville Inc.), were taken from the bone marrow of a black man 18 years old (PT-2501). At the time of delivery from the provider, the bone marrow-derived mesenchymal stem cells amounted to $1.6\times10^7$ cells (passage number 2), and were grown to 99% confluence for 2 hrs in a previously coated 10-cm plate (CELLstart™ CTS™, Gibco, USA) containing LONZA MSCBM (Mesenchymal Stem Cell Basal Medium) supplemented with 10% MCGS supplement+2% L-glutamine+0.1% GA-1000 in a 37° C. $CO_2$ incubator. Growth was carried out by passaging to passage number 3 in the same medium to secure the needed number of cells. FIG. 1A is a microphotograph image (×100) of bone marrow-derived mesenchymal stem cells at passage number 4.

EXAMPLE 2

Figure 1B:
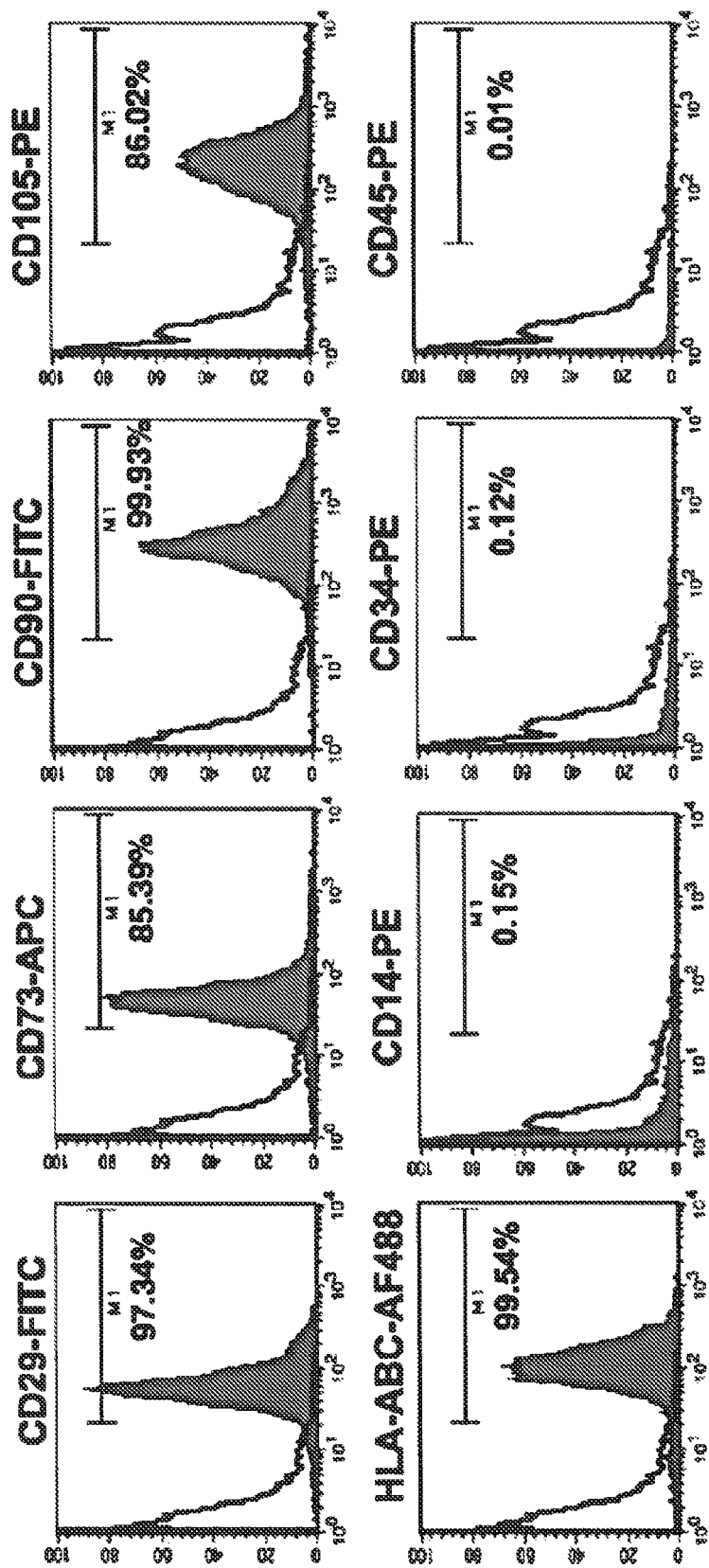

Characterization of Bone Marrow-Derived Mesenchymal Stem Cells by FACS (Fluorescence-Activated Cell Sorting) Analysis A majority (>98%) of the bone marrow-derived mesenchymal stem cells (P4) used in the present invention were found to have mesenchymal characteristics, as measured by FACS analysis using mesenchymal stem cell-specific cell surface markers (positive: CD29, CD73, CD90, CD105, HLA Class I-ABC, and negative: CD14, CD34, CD45). FIG. 1B gives the results of FACS analysis.

EXAMPLE 3

Figure 2A:
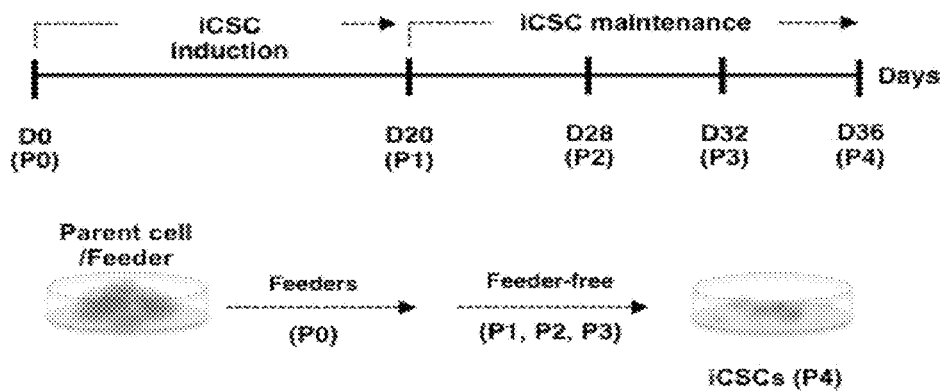
FIGS. 2A to 2F illustrate an induction method of cancer stem cells using human bone marrow-derived stem cells as feeder cells, and its results.
Figure 2B:
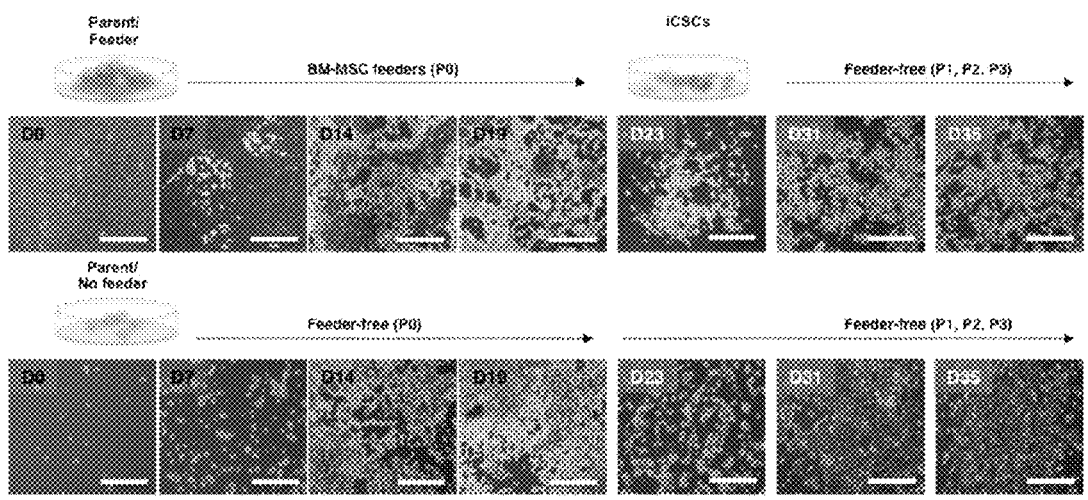

Induction of Human Immortalized Cells to Induced Cancer Stem Cells (iCSCs) Using BM-MSCs as Feeder Cells, and Growth of iCSCs While human bone marrow-derived stem cells served as feeder cells, less than 50 cells of each human immortalized cell line (HEK293, 293T, 293FT, Dermal papilloma, neural stem cell, L-132, U87-MG, SW480, A549, HeLa) were co-cultured according to the protocol shown in FIG. 2A for about 20 days to form colonies (FIG. 2B) which were sub-cultured by mechanical passaging. Media necessary for growing BM-MSCs of Example 1 and for inducing and growing BM-MSCs to iCSCs (induced cancer stem cells) are as follows:

1) medium for bone marrow-derived mesenchymal stem cells: LONZA MSCBM (Mesenchymal Stem Cell Basal Medium) +10% MCGS supplement+2% L-glutamine+0.1% GA-1000; and 2) medium for induced cancer stem cells: DMEM (high glucose, 25 mM) +8~10% FBS+2 mM L-glutamine+4 mM L-alanyl-glutamine+1% Penicillin-streptomycin.

EXAMPLE 4

Characterization of the iCSCs by Immunostaining

Figure 2C:
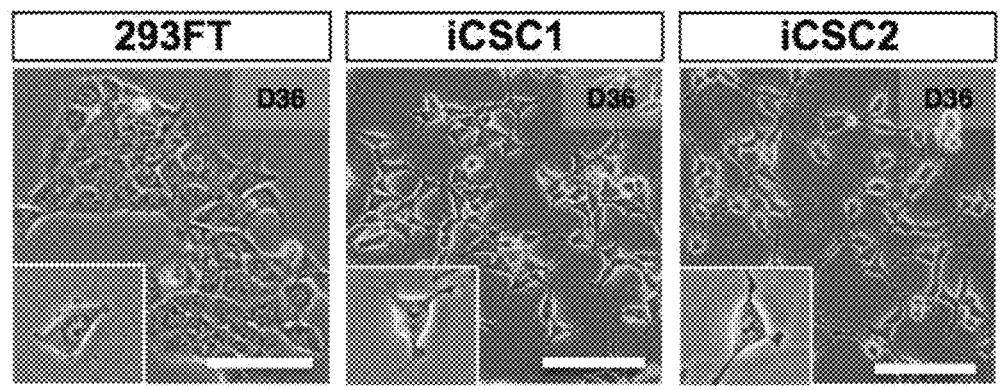
Figure 2D:
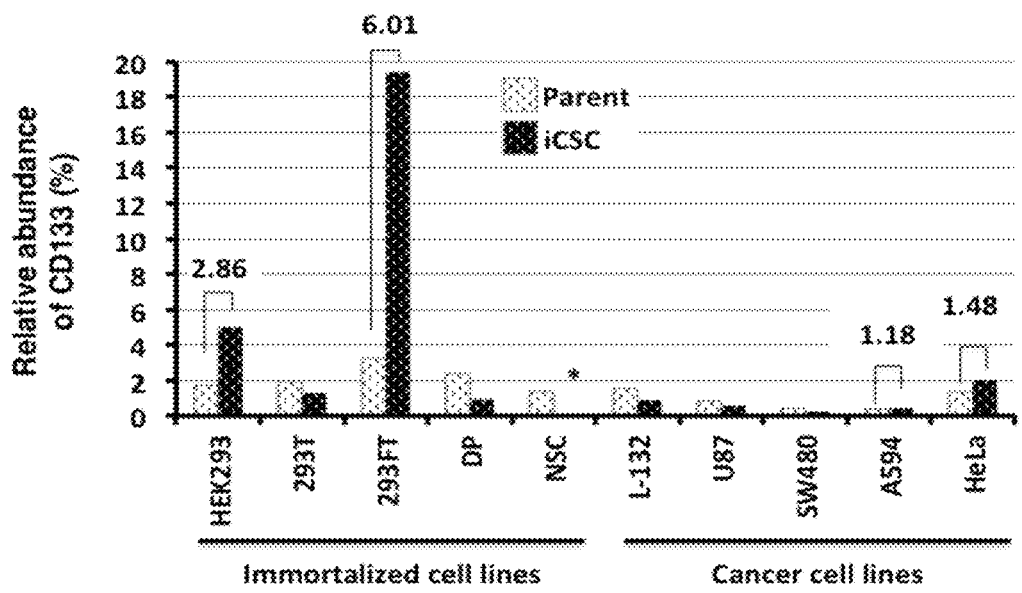

FIG. 2C shows microphotographic images (×100, at day 36) of the induced cancer stem cell lines (iCSC1, iCSC2) of the present invention derived from the human immortalized cell line (293FT). FIG. 2D is a graph of FACS analysis results showing the expression level of CD133 protein which reveals the efficiencies of induction to cancer stem cells from five human immortalized cell lines (HEK293, 293T, 293FT, Dermal papilloma or Neural stem cell) and from five human cancer cell lines (L-132, U87-MG, SW480, A549 or HeLa).

EXAMPLE 5

Figure 2E:
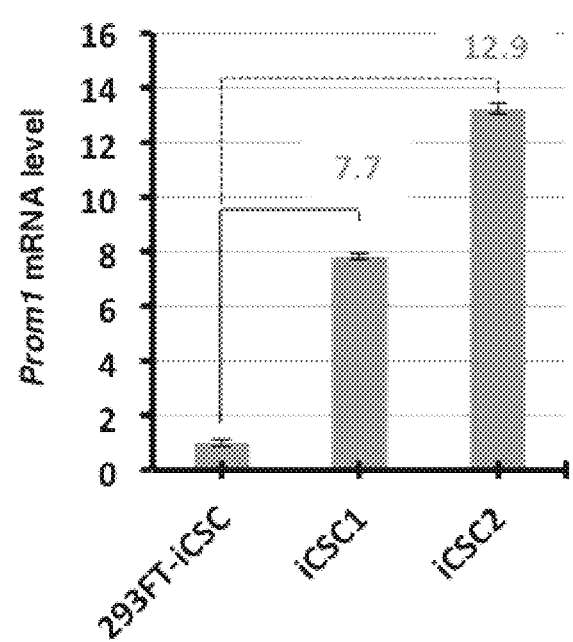

Characterization of the iCSCs by Real-Time PCR Real-Time PCR Analysis Showed the iCSC of the Present invention (FIG. 2C) increased expression levels of the markers (CD133: prom1) characteristic of neural stem cells and cancer stem cells (FIG. 2E).

EXAMPLE 6

DNA Profiling of 293FT Cells and iCSCs by STR Analysis

The parent cell line 293 FT was found to have the same genetic features as the cancer stem cells induced therefrom (iCSC), as measured by STR (short tandem repeat) analysis (Table 2).

TABLE 2

STR profile of 293FT and iCSC1, 2 cell lines

|  | Locus name | Chromosomal location | 293FT | iCSC1 | iCSC2 |
|---|---|---|---|---|---|
| 1 | Amelogenin | 23 | X, X | X, X | X, X |
| 2 | CSF1PO | 5q33.1 | 11, 12 | 11, 12 | 11, 12 |
| 3 | D13S317 | 13q22-q31 | 12, 12 | 12, 12 | 12, 12 |
| 4 | D16S539 | 16q24.1 | 9, 9 | 9, 9 | 9, 9 |
| 5 | D5S818 | 5q21-q31 | 8, 9 | 8, 9 | 8, 9 |
| 6 | D7S820 | 7q | 11, 12 | 11, 12 | 11, 12 |
| 7 | THO1 | 11p15.5 | 7, 9.3 | 9.3, 9.3 | 7, 9.3 |
| 8 | TPOX | 2q25.3 | 11, 11 | 11, 11 | 11, 11 |
| 9 | vWA | 12p13.31 | 16, 19 | 16, 19 | 16, 19 |
| 10 | D8S1179 | 8q24.13 | 12, 14 | 12, 12 | 12, 14 |
| 11 | D21S11 | 21q21.1 | 28, 30.2 | 30.2, 30.2 | 28, 30.2 |
| 12 | D3S1358 | 3p21 | 15, 17 | 15, 17 | 15, 17 |
| 13 | D2S1338 | 2q35 | 19, 19 | 19, 19 | 19, 19 |
| 14 | D19S433 | 19q12 | 15, 18 | 18, 18 | 15, 18 |
| 15 | D18S51 | 18q21.33 | 17, 17 | 17, 17 | 17, 17 |
| 16 | FGA | 4q28 | 23, 23 | 23, 23 | 23, 23 |

EXAMPLE 7

DNA Profiling of 293FT and iCSC by Karyotyping

Figure 2F:
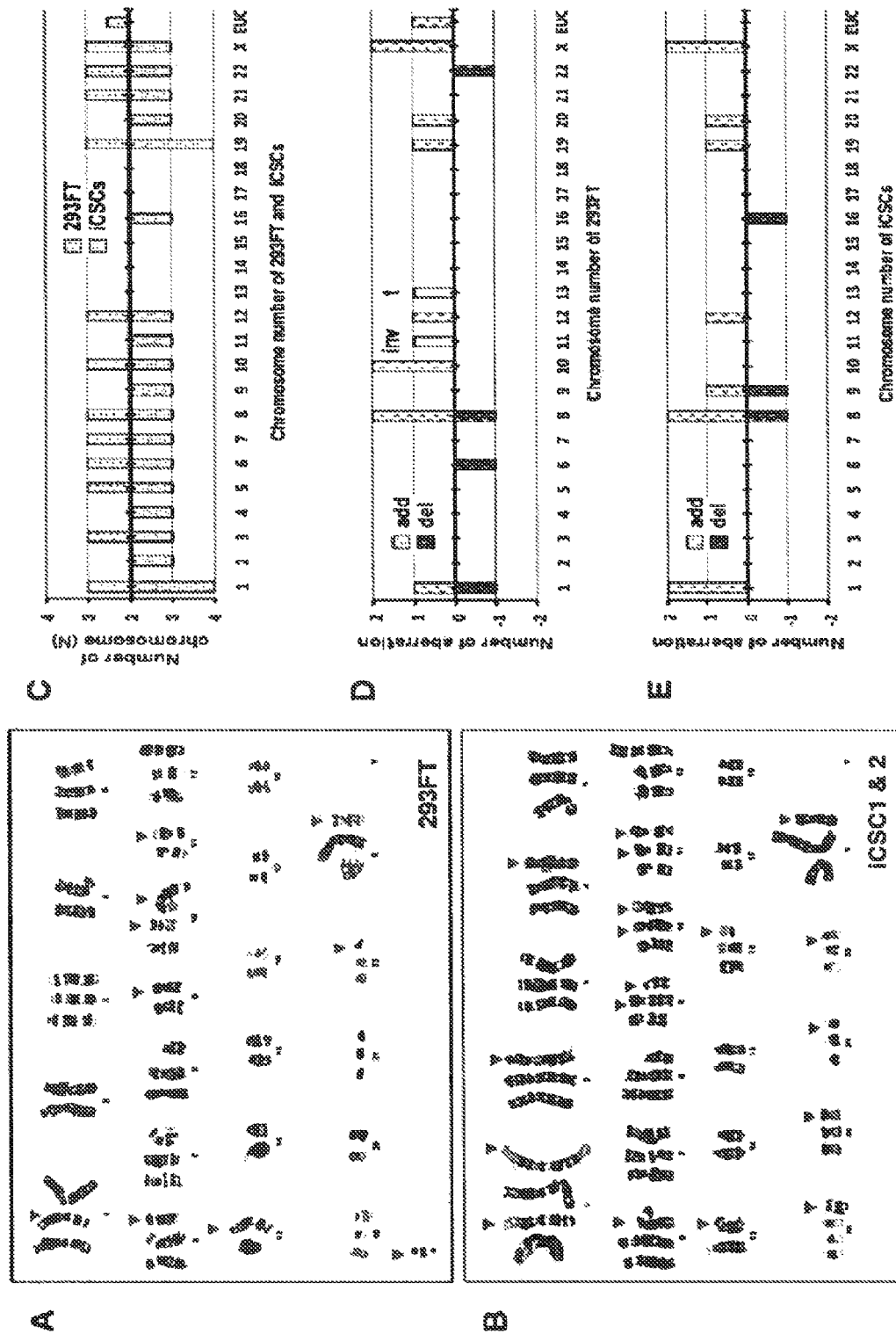

From karyotyping analysis of 293FT and iCSC, it was apparent that the iCSC increased in the total number of chromosomes by 6, compared to 2934FT (FIG. 2F: A, karyotyping of 293FT; B, karyotyping of iCSC; C, numbers of chromosomes of 293FT and iCSC, as measured by karyotyping), but decreased in structural chromosomal aberration, compared to 293FT (by 1 for addition; 1 for deletion; 1 for inversion; and 1 for translocation) (FIG. 2F: D, structural chromosomal aberrations of 293FT; E, structural chromosomal aberrations of iCSC).

EXAMPLE 8

Markers for Various Cancer Stem Cells by FACS Analysis

Figure 3:
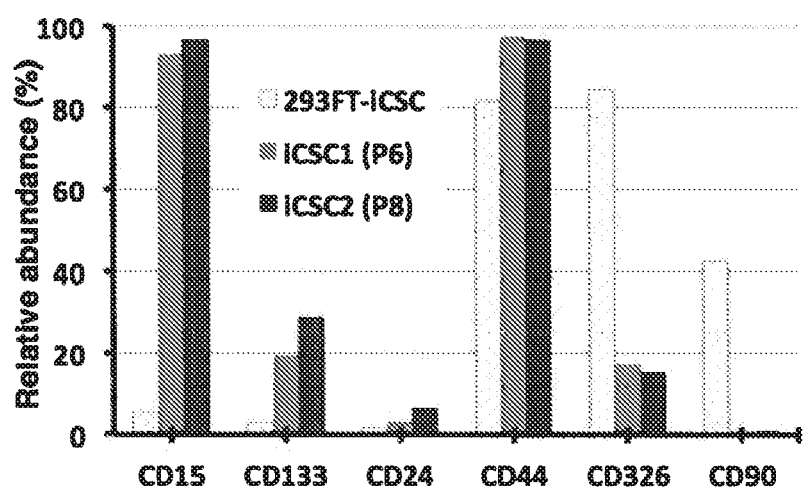
FIG. 3 is a graph comparing characteristics between human immortalized cell line (293FT) and 293FT-derived cancer stem cells (iCSC), indicating the existence of brain cancer stem cell markers and other cancer stem cell markers, as analyzed by FACS using known tissue-specific cancer stem cell markers (Table 3)

Expression levels of various cancer stem cell markers were measured (CD15, 92~96%; CD133, 19~28%; CD24, 3~6%; CD44, 96~97%; CD326, 15~17%; CD90, 0.7%). From the measurements, it was confirmed that brain cancer cell markers ($CD15^+$, $CD133^+$, CD441 shared high expression percentages (FIG. 3 and Table 3).

TABLE 3

| Tumor type | Cell surface markers |
|---|---|
| Brain | $CD15^+/CD133^+$ |
| Breast | $CD44^+/CD24^{Low/-}$ |
| Colon | $CD44^+/CD326^{High/+}$ |
| Kidney | $CD133^+$ |
| Head and neck | $CD44^+$ |
| Liver | $CD90^+$ |
| Lung | $CD133^+$ |
| Pancreas | $CD44^+/CD24^+/CD326^+$ |
| Prostate | $CD133^+$ |

EXAMPLE 9

Analysis for Various Neural Stem Cell Markers by Immunostaining and FACS

Figure 4A:
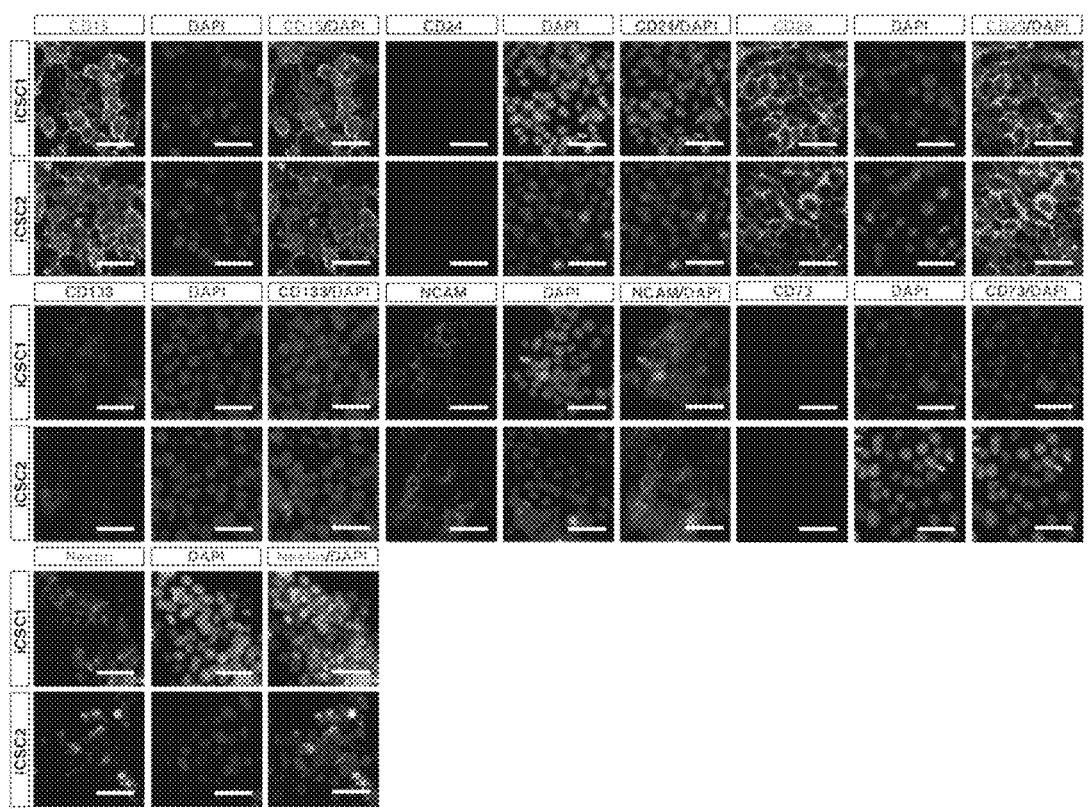
FIG. 4A shows the expression of various neural (brain cancer) stem cell markers in the 293FT-derived cancer stem cell line, as analyzed by immunostaining.
Figure 4B:
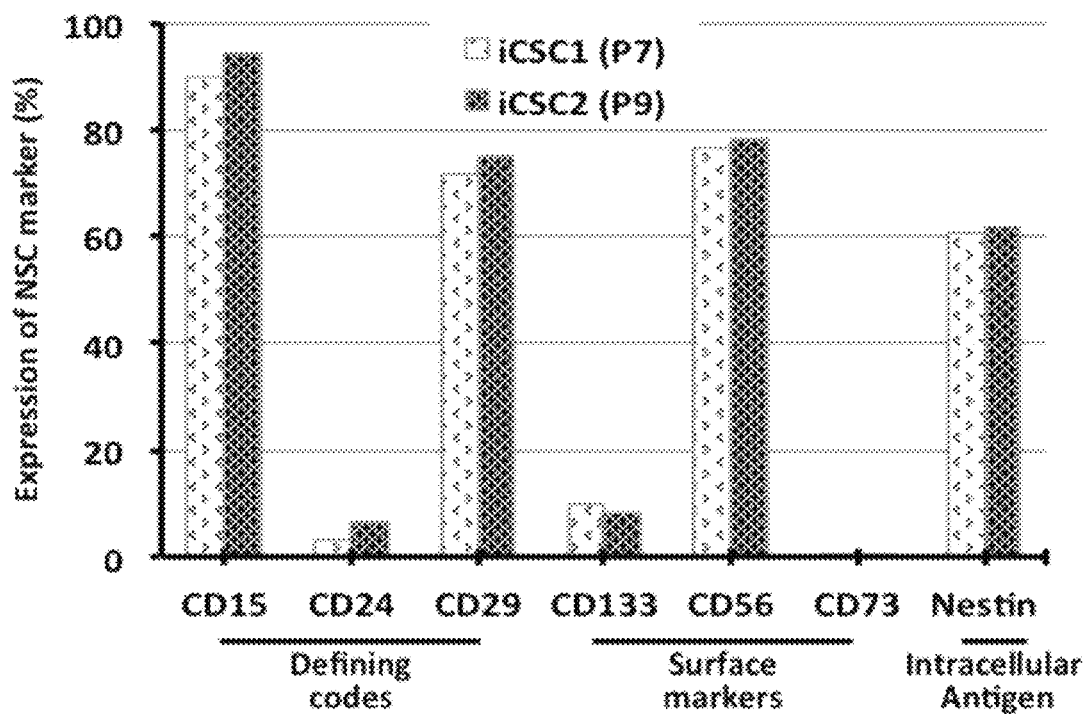
FIG. 4B shows the expression of neural stem cell markers in the 293FT-derived cancer cell line, as analyzed by FACS.

Immunostaining for various cancer stem cell markers (CD15, CD24, CD29, CD133, NCAM/CD56, CD73, Nestin) was carried out to identify features of neural stem cells ($CD15^+$, $CD24^{Low}$, $CD29^+$, $CD133^+$, $CD56/NCAM^+$, $CD73^-$, $Nestin^+$) (FIG. 4A). In addition, percent expression of neural stem cell markers were measured by FACS ($CD15^+$, 89 to 94%; $CD2^{Low}$, 3 to 6%; $CD29^+$, 71 to 74%; $CD133^+$, 7 to 9%; CD56/NCAM+, 76 to 78%; $CD73^-$, 0.12%; $Nestin^+$, 61~62%) (FIG. 4B).

EXAMPLE 10

Figure 5:
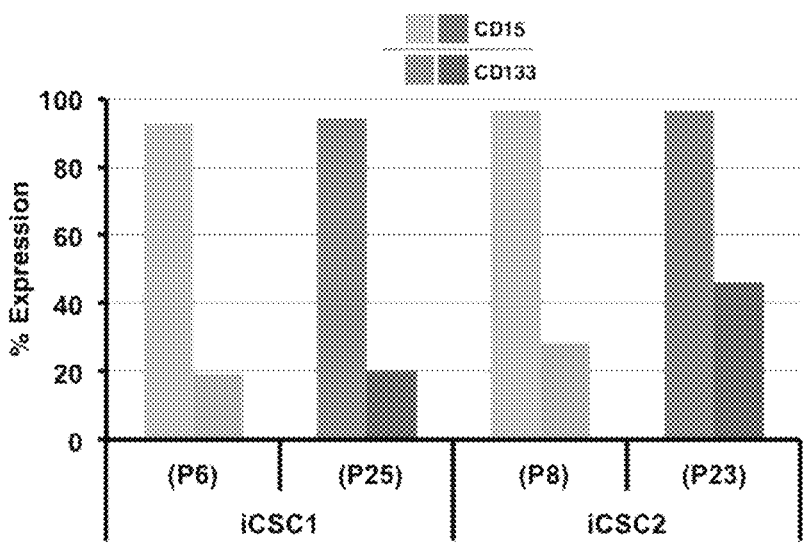
FIG. 5 shows the maintenance of the cancer stem cells even after long-time culture, as analyzed by FACS using CD15 and CD133 (see Table 4)

Change in Expression Percent of Brain Cancer Stem Cell Marker after Early and Late Passage Few differences in the expression percent of CD15 were detected between early and late passages (0.08 to 1.5%). CD133 expression was increased in late passages, compared to early passages (0.79 to 17.72%), whereas CD44 was expressed at a lower level in late passages than in early passages (31.27 to 52.84%) (FIG. 5 and Table 4).

TABLE 4

Percent Expression of Cancer Stem Cell Marker

| Cultured cells | Passages | Total $CD15^+$ | Total $CD133^+$ | Total $CD44^+$ | $CD15^+/CD133^+$ | $CD44^+/CD133^+$ | $CD15^+/CD44^+$ | $CD15^+/CD44^+/CD133^+$ | $CD15^-/CD44^-/CD133^-$ |
|---|---|---|---|---|---|---|---|---|---|
| 293FT | P6 | 5.51 | 3.03 | 81.39 | 2.03 | 2.35 | 4.71 | 1.64 | 17.52 |
| iCSC1 | P6 | 92.95 | 19.42 | 97.48 | 19.42 | 19.36 | 91.62 | 19.36 | 1.19 |
|  | P25 | 94.45 | 20.21 | 44.64 | 20.19 | 13.21 | 43.70 | 13.18 | 4.60 |
| iCSC2 | P8 | 96.63 | 28.59 | 96.63 | 28.59 | 28.42 | 94.36 | 28.42 | 1.11 |
|  | P23 | 96.55 | 45.31 | 65.36 | 46.26 | 35.66 | 64.53 | 35.62 | 2.61 |

EXAMPLE 11

Neurosphere Formation Ability and Characterization

Figure 6A:
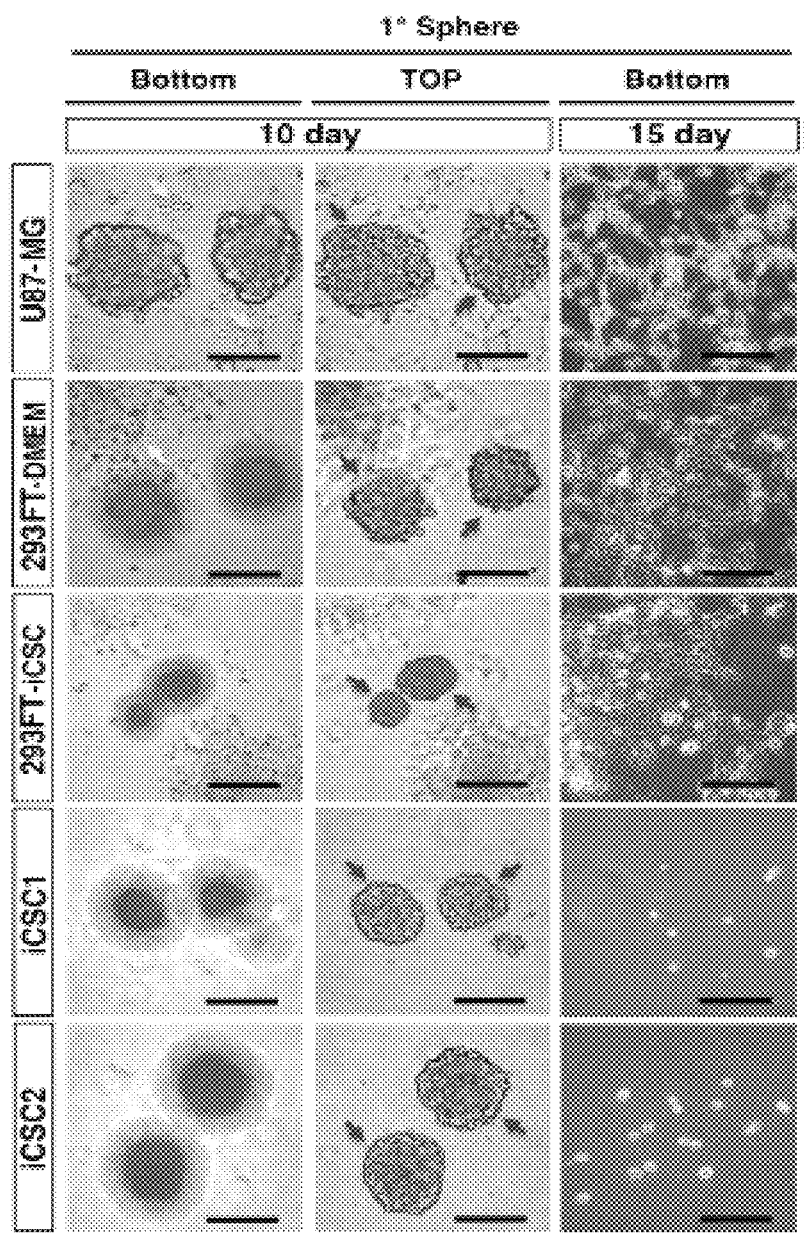
FIG. 6A shows the formation of neurospheres from the cancer stem cell lines (iCSC1, iCSC2), the immortalized cell line (293FT) and the human glioblastoma multiforme (U87-MG) in an induction medium (magnified 200 times)
Figure 6B:
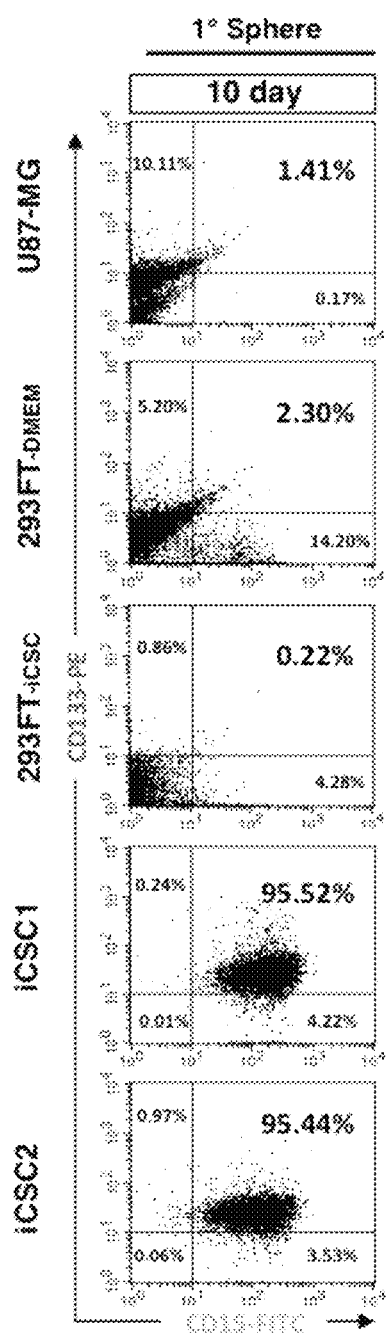
FIG. 6B shows the expression of CD15 and CD133 in the neurospheres (primary spheres) of FIG. 6A, as analyzed by FACS.
Figure 6C:
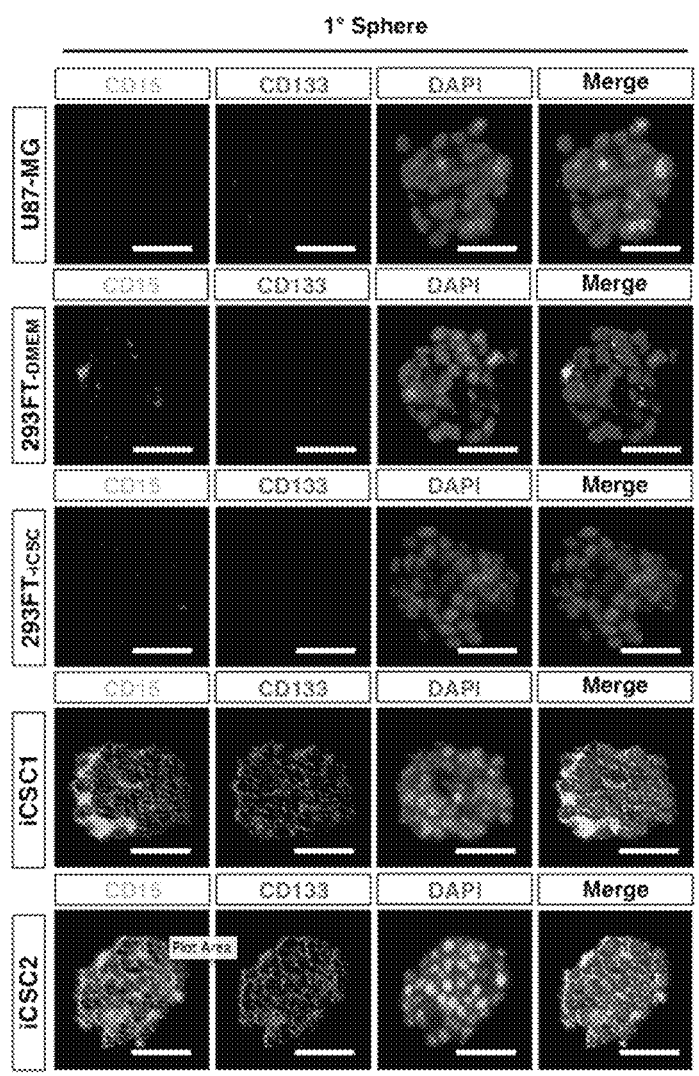
FIG. 6C shows the expression of CD15 and CD133 in the neurospheres (primary sphere) of FIG. 6A, as analyzed by immunostaining.
Figure 6D:
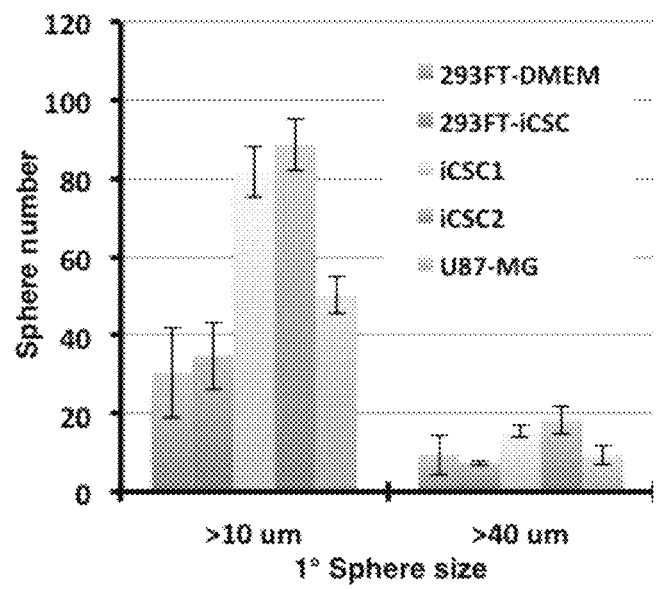
FIG. 6D is a graph in which the formation of neurospheres (primary spheres) of FIG. 6A is quantitatively analyzed.
Figure 6E:
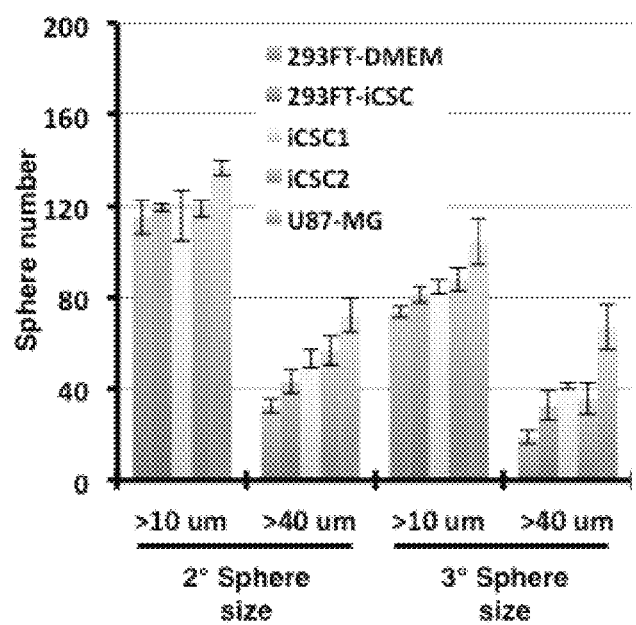
FIG. 6E is a graph in which the formation of secondary and tertiary spheres from the neurospheres (primary spheres) of FIG. 6A is quantitatively analyzed.

The cancer stem cells were induced to form neurospheres in DMEM/F-12 supplemented with 20 ng FGF and 20 ng EGF. As a result, iCSC was observed to have high ability to form neurospheres (FIGS. 6A, 6D, 6E), but to be unlikely to differentiate (FIG. 6A, Day 15). In the iCSC neurosphere (primary sphere), the expression level of the neural stem cell marker CD133 increased by more than 95%, with consequent increase in CD15$^+$/CD133$^+$ population (>95%) (FIG. 6D). After cryosection, immunostaining exhibited increased levels of CD15 and CD133 in iCSC (FIG. 6C).

EXAMPLE 12

Differentiation to Neural Cell from Primary Sphere

Figure 7A:
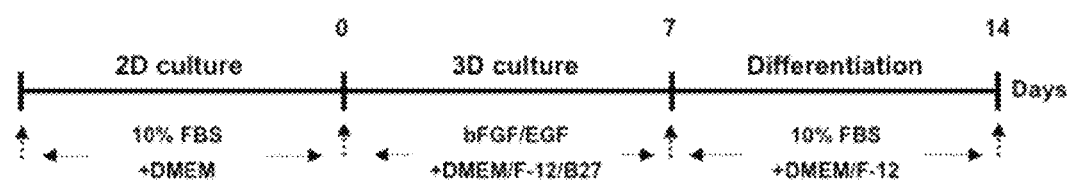
FIG. 7A is a schematic view of a protocol for differentiating the cancer stem cell line of the present invention to neural cells.
Figure 7B:
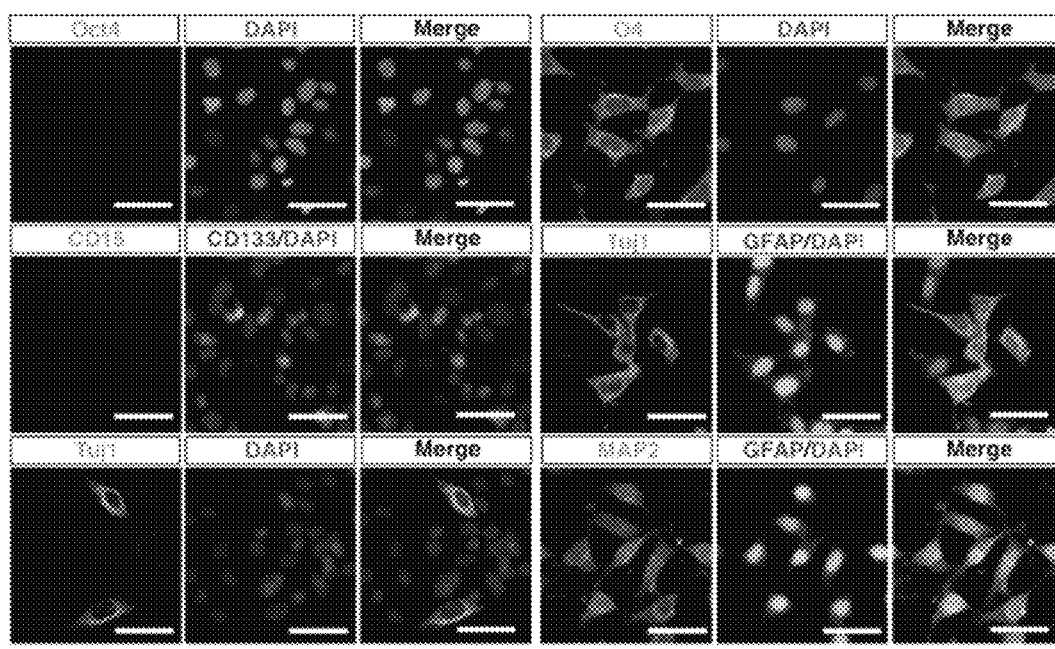
FIG. 7B shows the differentiation of neural cells from the cancer stem cells according to the protocol of FIG. 7A, as analyzed by immunostaining using various neural cell-specific markers.
Figure 7C:
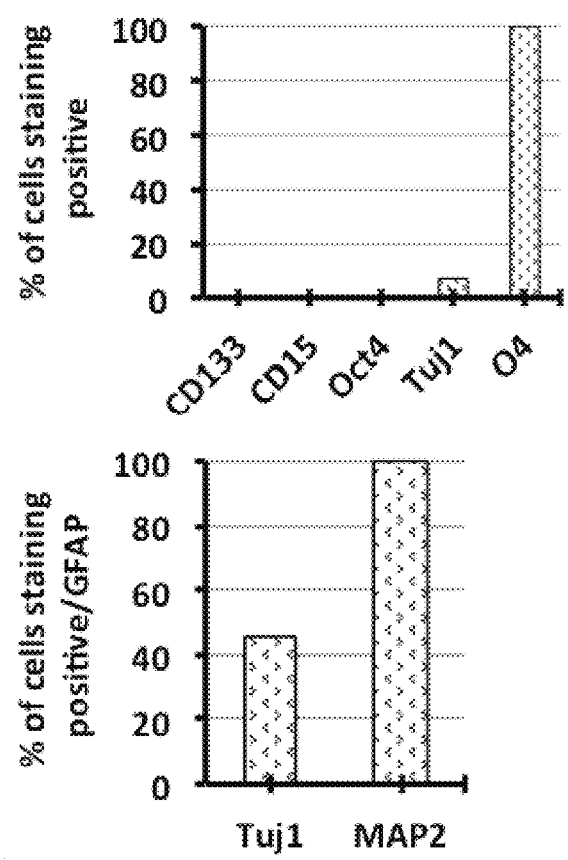
FIG. 7C shows quantitative representations of the results of FIG. 7B.

The primary sphere, after being formed (Day 7), was induced for 7 days to undergo differentiation in a differentiation medium supplemented with 10% FBS (FIG. 7A), followed by immunostaining analysis for stem cell markers (Oct4, CD15, CD133) and neural cell markers (Tuj1, O4, GFAP, MAP2). The stem cell markers disappeared (Oct4, 0%; CD15, 0%; CD133, 0%) while the neural cell markers were expressed at elevated levels (Tuj1, 7%; O4, 100%; GFAP, 100%; MAP2, 100%) (FIG. 7B). In addition, percentages of cells positive to Tuj1$^+$ and MAP2$^+$ were measured to be 45% and 100%, compared to GFAP$^+$, respectively (FIG. 7C).

EXAMPLE 13

Figure 8A:
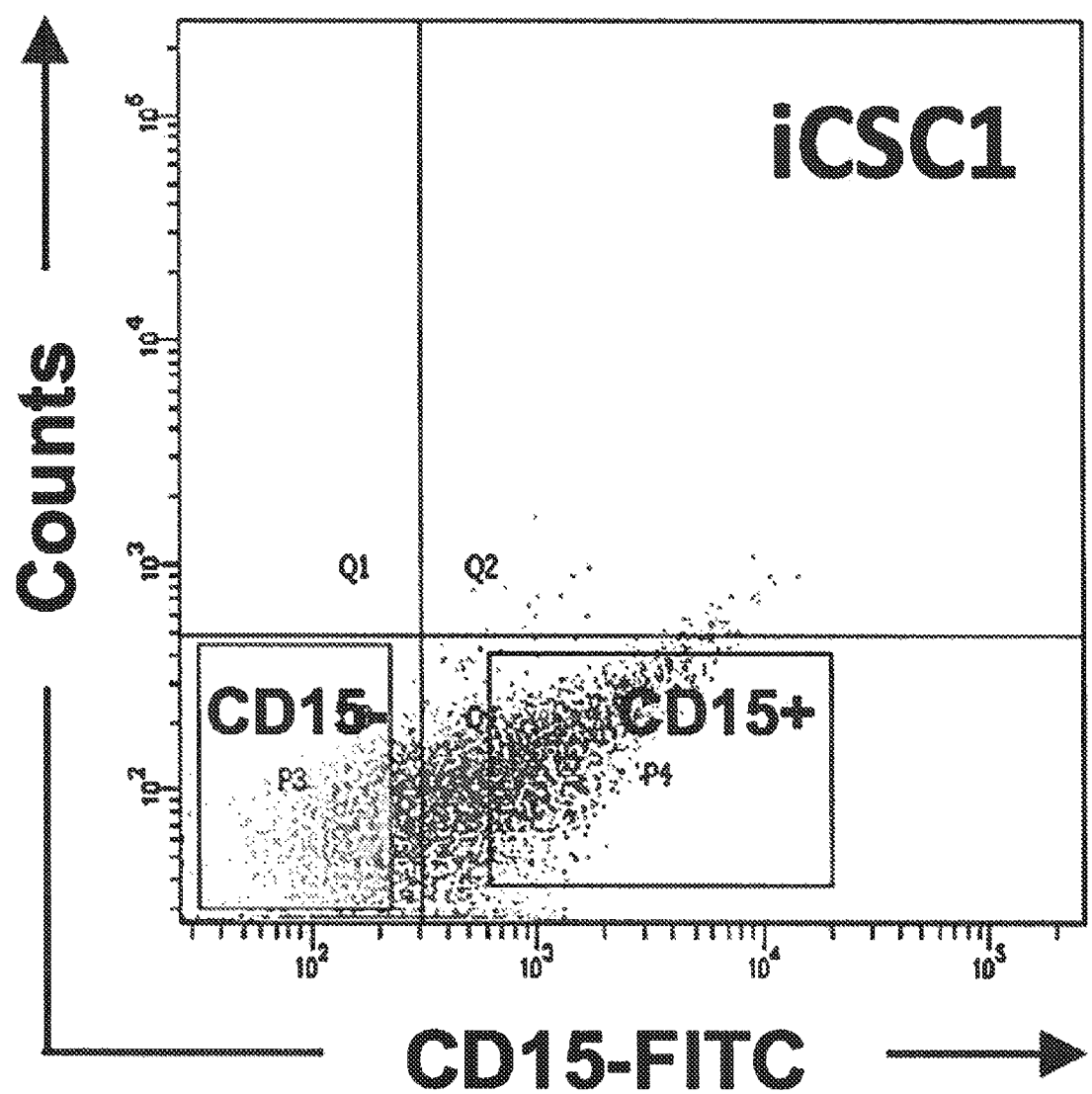
FIG. 8A shows the sorting of the cancer stem cells (iCSC1) of the present invention to $CD15^+$ and $CD15^-$ cells by FACS.

Oncogenicity of iCSCs iCSC1 was sorted to CD15$^+$ and CD15$^-$ cells by FACS (FIG. 8A). iCSC (unsorted), CD15$^+$ cells, CD15$^-$ cells, and 293FT cells were subcutaneously injected to respective immunosuppressive mice (BALE/c nu/nu) which were then monitored for tumor formation. Groups injected with iCSC (unsorted) and CD15$^+$ cells developed tumors at the same ratio (average percent of cancer stem cells present=Number of cancer stem cells/total cell population=1/333 to 1/134, P=0.995) while iCSC (unsorted) and CD15$^-$ cells exhibited different tumorigenicity (average percent of cancer stem cells present=Number of cancer stem cells/total cell population=1/333 to 1/28,004; P=2.36e$^{-9}$) (FIG. 8B).

Figure 8C:
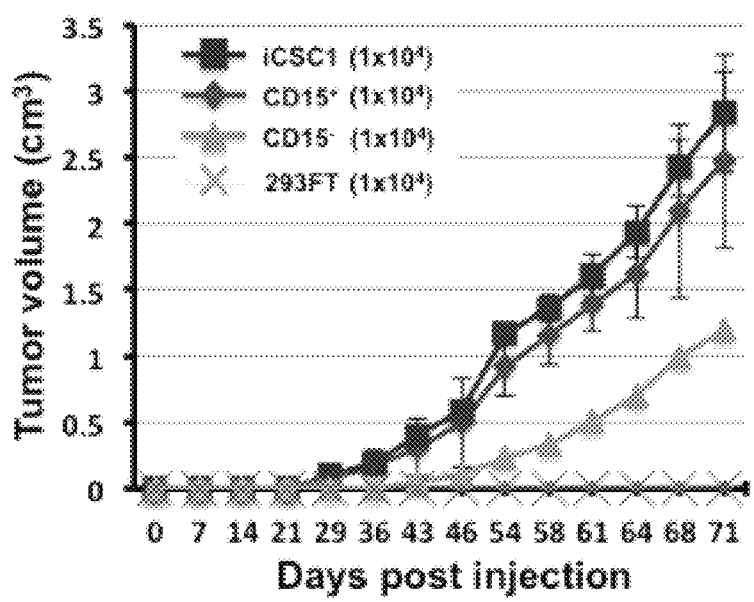
FIG. 8C is a graph showing the oncogenicity of iCSC1, $CD15^+$, $CD15^-$, and 293FT cells after subcutaneous injection at the same dose ($1 \times 10^4$ cells) to immunosuppressive mice (BALE/c nu/nu)
Figure 8D:
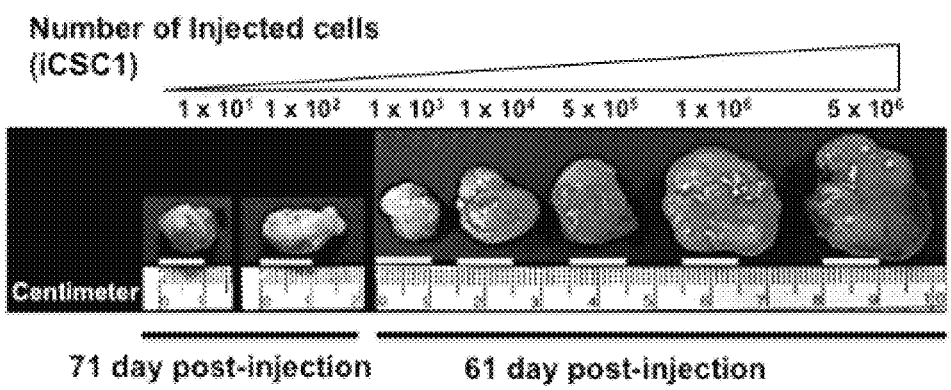
FIG. 8D shows sizes of tumors formed by subcutaneously injecting various numbers ($1 \times 10^1 \sim 5 \times 10^6$ cells) of iCSC (unsorted) to immunosuppressive mice (BALE/c nu/nu)
Figure 8E:
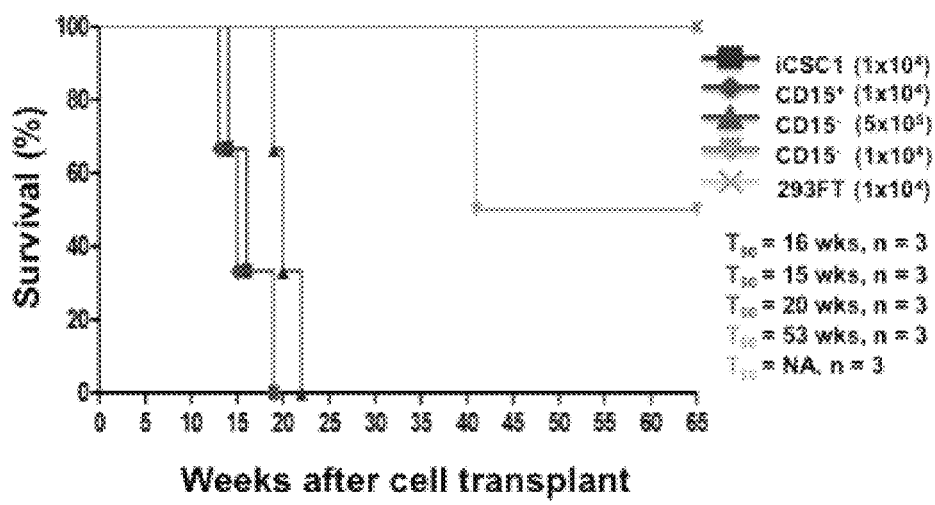
FIG. 8E is a graph showing survival rates of mice injected with various cells.

The same number (1×10$^4$ cells) of iCSC1, CD15$^+$, CD15$^-$, and 293FT cells was subcutaneously injected to respective immunosuppressive mice (BALE/c nu/nu) which were then monitored for tumor formation. After injection with CSC1 (unsorted) and CD15$^+$ cells, it took 46 days for tumor to develop to a volume of 0.5 cm$^3$ while CD15$^-$ cells formed such tumor 61 days post-injection. However, no tumor was found in the mice injected with 293FT cells even after 71 days of injection (FIG. 8C). The iCSC (unsorted)-induced tumor increased in volume in a dose-dependent manner (FIG. 8D). Survival rates after cell transplantation were the lowest in the groups of CD15$^+$ and iCSC1 (unsorted), and exhibited dose dependency as is apparent from the data of the group of CD15$^-$ cells (5×10$^5$ cells, T$_{50}$=20 weeks; 1×10$^4$ cells, T$_{50}$=53 weeks). The group transplanted with 293 FT (1×10$^4$ cells) survived even after 65 weeks (455 days) of transplantation because no tumors were formed (FIG. 8E).

EXAMPLE 14

Figure 9A:
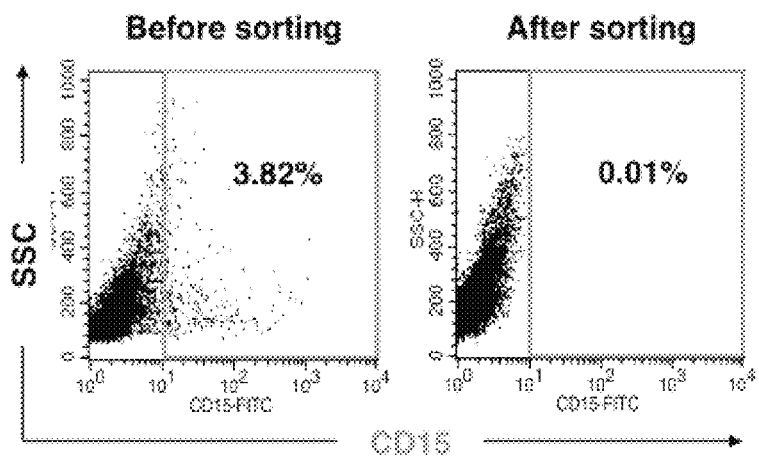
FIG. 9A shows the existence of a side-population of $293FT^{CD15+}$ cells (3.82%) in 293FT cells, as analyzed by FACS (Fluorescence Activated Cell Sorting), and the identification of the remainder cells resulting from the removal of $293FT^{CD15+}$ cells (3.82%) by MACS (Magnetic-activated cell sorting) as $293FT^{CD15-}$ cells (CD15, 0.01%), as analyzed by FACS.
Figure 9B:
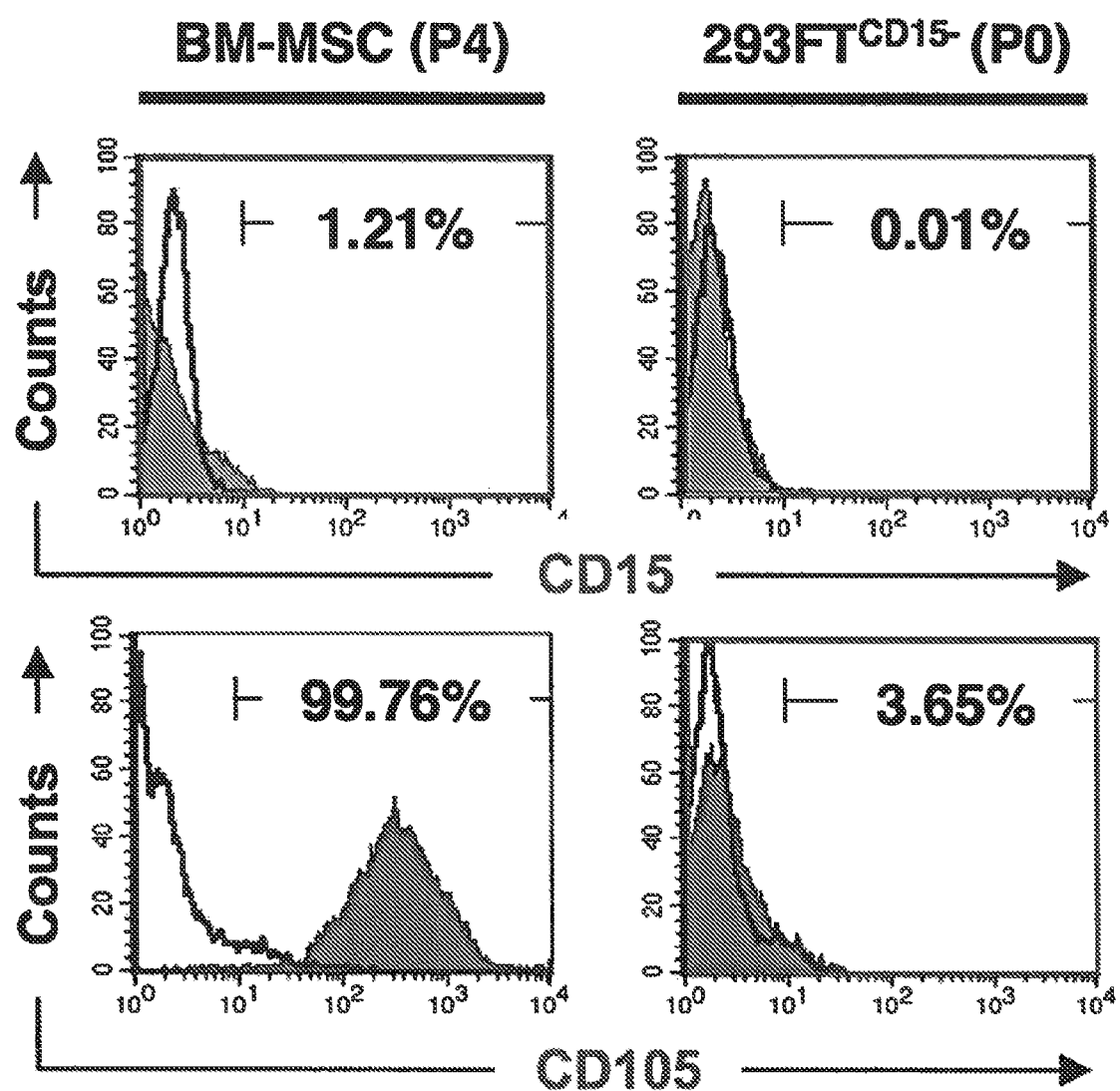
FIG. 9B shows that human BM-MSC serving as feeder cells, expressed, for the most part, the mesenchymal stem cell marker CD105 (99.76%), but little CD15 (1.21%), and that the $293FT^{CD15-}$ cells sorted in FIG. 9A (Passage number 0) expressed CD15 and CD105 at a level of 0.01% and 3.65%, respectively, as measured by FACS.
Figure 9C:
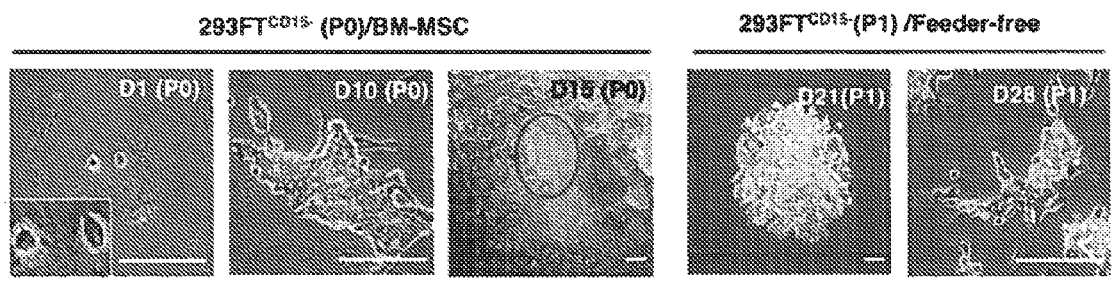
FIG. 9C shows the procedure of inducing cancer stem cells by co-culturing the $293FT^{CD15-}$ cells (passage number 0) isolated in FIG. 9A with the feeder cells (human BM-MSC, Passage number 4) for 20 days by microphotography. On Day 20 (passage number 0), central colonies (ultradense cell population) of the cell clumps were physically detached under microscopic observation, and subcultured in the absence of feeder cells (passage number 1)
Figure 9D:
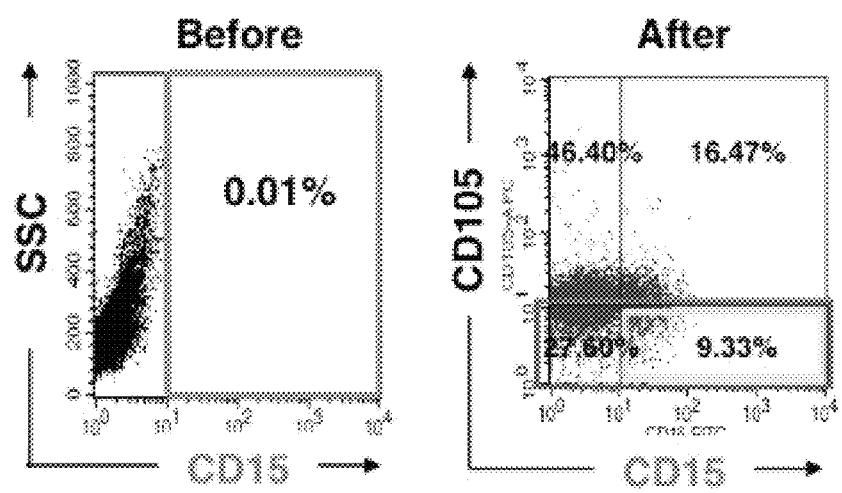
FIG. 9D shows FASC results after the co-cultured cells of FIG. 9C were detached from plates using trypsin on Day 20.
Figure 9E:
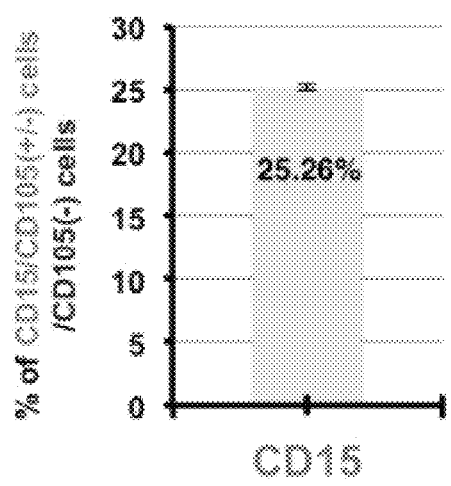
FIG. 9E is a graph of the induction efficiency analyzed by the FACS of FIG. 9C, showing transformation from $293FT^{CD15-}$ (0.01%) to $293FT^{CD15+}$ (25.8%)
Figure 9F:
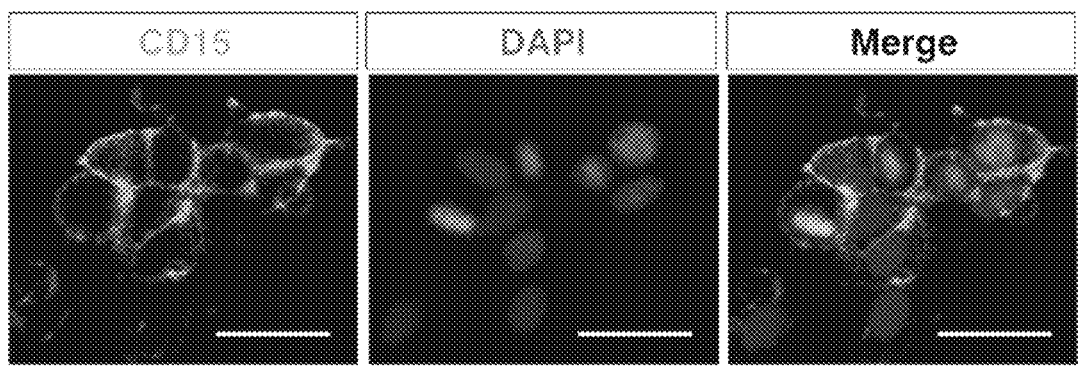
FIG. 9F shows the expression of CD15, a marker for brain cancer stem cells, in the cells which are grown from the $293FT^{CD15-}$ derived cancer stem cells of FIG. 9C through passages, as analyzed by immunostaining.
Figure 9G:
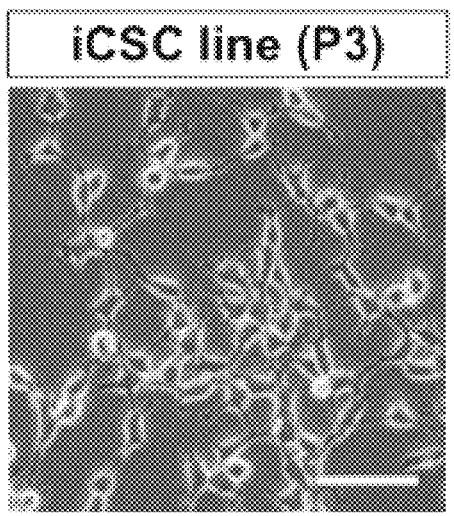
FIG. 9G shows $293FT^{CD15-}$ derived cancer stem cells grown by passages (Passage number 3) after induction, isolation and growth in FIG. 9C (magnified 200 times).

Analysis for Cancer Stem Cell Derived from Immortalized Cell Line after Removal of Cells Positive to Cancer Stem Cell Marker Out of 293FT cells, the side-population of 293FT CD15$^+$ (3.82%) cells were removed by MACS, and the remaining cells were identified to be CD15$^-$ (CD15$^+$, 0.01%) by FACS analysis (FIG. 9A). Human bone marrow-derived mesenchymal stem cells (passage number 4), which were used as feeder cells in the present invention were examined for CD15 and CD105 expression. BM-MSC expressed, for the most part, the mesenchymal stem cell marker CD105 (99.76%), but little CD15 (1.21%). In addition, the 293FT CD15$^-$ cells sorted in FIG. 9A (Passage number 0) were observed to express CD15 and CD105 at a level of 0.01% and 3.65%, respectively, as measured by FACS (FIG. 9B). While human bone marrow-derived mesenchymal stem cells (passage number 4) served as feeder cells, 293FT CD15$^-$ cells were cultured for 20 days to induce cancer stem cells (FIG. 9C). On Day 20 after the induction of cancer stem cells (passage number 0), the co-cultured cells were detached from plates using trypsin, and immunostained against the BM-MSC-specific marker CD105 and cancer stem cell-specific marker CD15, followed by FASC analysis (FIG. 9D). CD105$^+$ cells (BM-MSC) were observed to account for 62.87% (=46.40%+16.47%) of the total population (BM-MSC+293FT, 100%) while the remainder 36.93% (=27.60%+9.33%) corresponded to CD105$^-$ cells (293FT). Of these cells, 9.33% was accounted for by CD15/CD105$^{(+/-)}$ cells (293FT) which were those transformed to cancer stem cells according to the present invention, with an induction efficiency of 25.26% (% No. of cancer stem cells=% No. of CD15/CD105$^{(+/-)}$ cells=No. of CD15/CD105$^{(+/-)}$ cells/No. of CD105$^-$ cells=9.33/36.93) (FIG. 9E). In addition, the cancer stem cells which were maintained (passage number 1) after induction from 293FT CD15$^-$ cells were observed to express CD15, as measured by immunostaining (FIG. 9F). After growth, the cells, i.e. iCSC3 (Passage number 3) exhibited the same morphological features as in iCSC1 and iCSC2 (FIG. 9G).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The present invention enables cancer stem cells that are low in the level of structural chromosomal aberration and excellent in oncogenicity to be readily generated. The method of the present invention is effectively applicable to the development of anti-cancer drugs and personalized drugs.

What is claimed is:

1. A method for generating a cancer stem cell line from an immortalized 293FT cell line, comprising:
   co-culturing an immortalized 293FT cell line and mesenchymal stem cells in an induction medium, with the mesenchymal stem cells serving as feeder cells, for sufficient time to generate cancer stem cells characterized by neural stem cell markers CD15+ and CD 133+, and sub-culturing same to produce CD15+ and CD 133+ cells as said cancer stem cell line,
   wherein the induction medium comprises FBS, L-glutamine, L-alanyl-glutamine and high-glucose DMEM.

2. The method of claim 1, wherein the high-glucose DMEM glucose concentration is in a range of from 10 to 100 mM.

3. The method of claim 1, wherein the co-culturing is carried out for a period of from 16 to 20 days.

4. The method of claim 1, wherein the immortalized 293FT cell line decreases in accumulated structural chromosomal aberration (chromosomal instability), or increases in chromosomal mutation by the co-culturing.

5. The method of claim 1, wherein the cancer stem cells characterized by neural stem cell markers CD15+ and CD 133+ are sub-cultured to a passage number at which the CD15+ and CD 133+ cells constitute more than 90% of total cells.

6. The method of claim 1, wherein the cancer stem cell line possesses at least one of the following characteristics:
 (a) being immunologically positive to the neural stem cell markers CD56 (NCAM), CD29 (Integrin beta1), Nestin, CD24 (Small cell lung carcinoma cluster 4 antigen) and CXCR4 (chemokine (C-X-C motif) receptor 4); and negative to the mesenchymal stem cell marker CD73 (Ecto-5'-Nucleotidase);
 (b) no appearance of differentiated cells upon suspension culture;
 (c) the appearance of dendrites, morphologically characteristic of neural cells, having round and streamlined nuclei that are large in comparison to whole cells in an FBS-supplemented medium;
 (d) the oncogenicity that even as few as 10 cells can form tumor in immune-suppressed mice (BALB/c nu/nu); and
 (e) differentiation into neural cells in an induction medium.

7. The method of claim 6, wherein the cancer stem cell line is maintained for an extended period of time by a plurality of passages in an adherent culture manner in a medium supplemented with FBS.

8. The method of claim 6, wherein the cancer stem cell line is maintained for an extended period of time by a plurality of passages in a suspension culture in a medium devoid of FBS.

9. The method of claim 8, wherein the medium devoid of FBS further comprises bFGF and EGF.

10. The method of claim 8, wherein CD 133, serving as a marker for neural stem cells, is expressed at an elevated level by the suspension culture, thus making the CD15+ and CD 133+ cells account for more than 90% of total cell counts.

* * * * *

UNITED STATES PATENT AND TRADEMARK OFFICE
CERTIFICATE OF CORRECTION

PATENT NO.       : 9,540,614 B2                        Page 1 of 1
APPLICATION NO.  : 14/222697
DATED            : January 10, 2017
INVENTOR(S)      : Sunghoi Hong et al.

It is certified that error appears in the above-identified patent and that said Letters Patent is hereby corrected as shown below:

In the Specification

Column 4, Line 8: "(BALE/c nu/nu)" should be --(BALB/c nu/nu)--.

Column 4, Line 15: "(BALE/c nu/nu);" should be --(BALB/c nu/nu);--.

Column 4, Line 18: "(BALE/c nu/nu);" should be --(BALB/c nu/nu);--.

Column 6, Line 59: "(BALE/c nu/nu);" should be --(BALB/c nu/nu);--.

Column 11, Line 41: "(BALE/c nu/nu)" should be --(BALB/c nu/nu)--.

Column 11, Line 52: "(BALE/c nu/nu)" should be --(BALB/c nu/nu)--.

Column 11, Line 54: "CSCl" should be --CSC1--.

In the Claims

Column 13, Line 19: "(Integrin betal)," should be --(Integrin beta1),--.

Signed and Sealed this
Twenty-eighth Day of February, 2017

Michelle K. Lee
*Director of the United States Patent and Trademark Office*